United States Patent [19]

Gillespie

[11] Patent Number: 5,114,686
[45] Date of Patent: May 19, 1992

[54] CONTACT LENS DISINFECTION UNIT WITH INVERTIBLE LENS HOLDING BASKETS

[75] Inventor: Peter J. Gillespie, Norcross, Ga.

[73] Assignee: Ciba-Geigy Corporation, Hawthorne, N.Y.

[21] Appl. No.: 324,539

[22] Filed: Mar. 16, 1989

[51] Int. Cl.⁵ .................................................. A61L 2/18
[52] U.S. Cl. ..................................... 422/300; 422/301; 206/5.1; 206/438; 220/208; 220/209
[58] Field of Search ........................ 422/292, 300, 301; 206/5.1, 438; 220/208, 209; 425/440, 439

[56] References Cited

U.S. PATENT DOCUMENTS

| | | | |
|---|---|---|---|
| 2,967,607 | 3/1960 | Hollinger | 206/5.1 |
| 3,640,294 | 2/1972 | Piccolo | 206/5.1 |
| 4,011,941 | 3/1977 | Parsons | 206/5.1 |
| 4,126,345 | 11/1978 | List | 294/1 |
| 4,143,116 | 3/1979 | Meltzer | 422/116 |
| 4,158,411 | 6/1979 | Hall | 206/531 |
| 4,228,136 | 10/1980 | Thomas | 422/307 |
| 4,361,536 | 11/1982 | Leopardi | 422/33 |
| 4,396,583 | 8/1983 | LeBoeuf | 422/301 |
| 4,520,923 | 6/1985 | Waldman | 206/5.1 |
| 4,582,076 | 4/1986 | Prat | 422/300 X |
| 4,637,919 | 1/1987 | Ryder et al. | 422/300 |
| 4,750,610 | 6/1988 | Ryder | 422/300 X |
| 4,826,001 | 5/1989 | Castillo | 206/5.1 |
| 4,838,413 | 6/1989 | Monestere | 206/5.1 |
| 4,889,693 | 12/1989 | Su et al. | 422/301 X |
| 4,890,729 | 1/1990 | Ranalletta | 206/5.1 |
| 4,956,156 | 9/1990 | Kanner et al. | 422/300 |

*Primary Examiner*—Lynn Kummert
*Attorney, Agent, or Firm*—Wenderoth, Lind & Ponack

[57] ABSTRACT

A contact lens holding unit constituted by: a container; a cap detachably mounted on the container; a lens holder mounted on the container and extending into the container, the lens holder including at least one lens basket for receiving a contact lens therein for holding the contact lens with the surfaces thereof exposed to the space around the holder, the lens basket being invertible from a concave position in which it holds a lens with the convex side against the lens basket to a convex position in which it pushes the lens out of the basket. The unit can be converted to a lens disinfection unit by the addition of a catalyst block positioned in the container, preferably on the lens holder, whereby when a disinfection solution which is decomposed is placed in the container for disinfecting a lens held in the lens holder, the catalyst block begins decomposition of the solution.

27 Claims, 9 Drawing Sheets

CONTACT LENS DISINFECTION UNIT WITH INVERTIBLE LENS HOLDING BASKETS

The present invention relates to a contact lens disinfection unit, and more particularly to such a unit in which contact lenses are held in invertible baskets as a disinfecting solution is circulated thereover for disinfecting them, and from which they can then be easily removed.

BACKGROUND OF THE INVENTION

It is particularly important that so-called soft contact lenses be kept sterile, because they tend to cause infections in the eye if they are not periodically disinfected.

A lens disinfection unit has been developed which avoids past methods of disinfecting such lenses which involved such cumbersome steps as boiling them for a predetermined length of time, or alternatively immersing them in a disinfecting solution, particularly hydrogen peroxide solutions, removing them from the solution, and immersing them again in a neutralizing solution or a rinsing solution. The newly developed lens disinfection unit also avoids such difficulties as the user forgetting whether a disinfecting solution and a neutralizing or rinsing solution, all of which are simple clear solutions, has been used, particularly where the lenses are immersed in the disinfecting solution and left standing for a period of time, during which the user forgets whether the lenses have been neutralized or rinsed. Needless to say, it is extremely dangerous to insert into the eye a contact lens which has been removed directly from a hydrogen peroxide disinfecting solution, since such a disinfecting solution is highly irritating to the eye.

Such newly developed contact lens disinfection unit has a container with a cap detachably mounted thereon, and a lens and catalyst block holder mounted on and depending from the cap and extending into the container when the cap is mounted on the container. The holder has lens receiving baskets therein for receiving a pair of contact lenses for holding the contact lenses with the surfaces thereof exposed to the space around the holder, and means is provided for holding a catalyst block on the holder in a position for circulation of a disinfecting solution from the space around the holder and over the lenses in the baskets and over the catalyst block.

However, this lens disinfection unit can be cumbersome to use because while the insertion of the lenses, which are quite small, into the baskets can be relatively easy, removal from the baskets can be very difficult.

There is a need for a lens disinfection unit which has lens holding means which is easy to use and from which it is particularly easy to remove the lenses.

OBJECTS AND BRIEF SUMMARY OF THE INVENTION

It is an object of the present invention to provide a contact lens disinfection unit for use with a contact lens disinfecting solution in which it is simple and easy to place the lenses into the lens holding baskets and to remove the lenses therefrom.

A contact lens holding unit according to the invention comprises a container, a cap detachably mounted on said container, and a lens holder mounted in said container and extending into said container, said lens holder including at least one lens basket for receiving a contact lens therein for holding the contact lens with the surfaces thereof exposed to the space around said holder, said lens basket being invertible from a concave position in which it holds a lens with the convex side against the lens basket to a convex position in which it pushes the lens out of the basket. The lens holding unit can further having a catalyst block positioned in the container, whereby when a disinfection solution which is decomposed is placed in said container for disinfecting a lens held in said lens holder, said catalyst block begins decomposition of said solution.

BRIEF DESCRIPTION OF THE DRAWINGS

The invention will be described in further detail in connection with the accompanying drawings, in which.

DETAILED DESCRIPTION OF THE DRAWINGS

Figure 1:
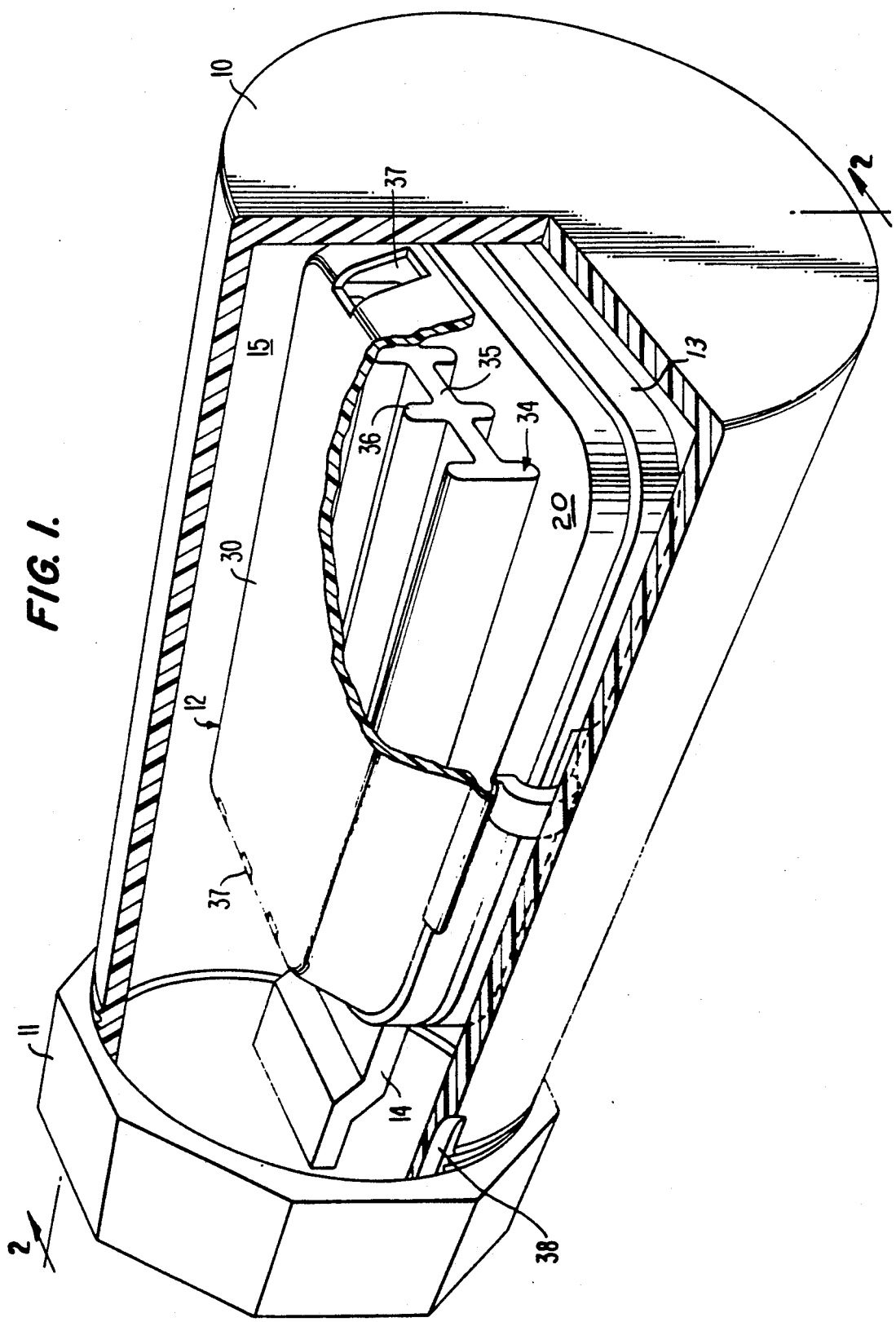
FIG. 1 is a perspective view, partly broken away, of a contact lens disinfection unit according to one embodiment of the invention.

The contact lens disinfection unit according to a first embodiment as shown in FIGS. 1-6, has a container 10, here shown as a cylindrical plastic container with a threaded neck, and a cap 11 detachably mounted on the container 10. In the embodiment shown, the attachment is by means of conventional threaded engagement, but any other conventional type of engagement, such as a snap fit, can be employed. Further, while the container is shown as being cylindrical, it can have any other convenient shape as desired.

A lens and catalyst block holder 12 is provided which is a base member 13 from which a stem 14 extends. The stem is mounted on the underside of the cap 11, so that with the container 10 in an erect position, the lens and catalyst block holder 12 depends from and extends into the container. The size of the container is such that a space 15 is left around the periphery of the lens and catalyst block holder 12 for holding a disinfecting solution.

The base member 13 has a pair of holes 16 therethrough which contain a pair of lens engaging means in the form of lens receiving baskets 21 which will be described more in detail hereinafter.

Figure 2:
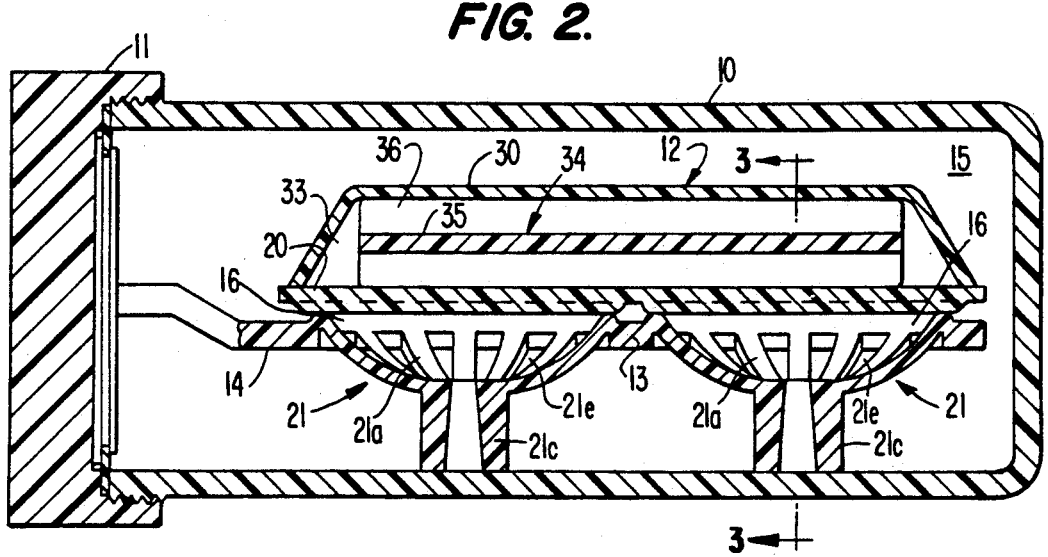
FIG. 2 is a sectional view taken along line 2—2 of FIG. 1.

The lens and catalyst block holder further comprises a top member 20, and the base member 13 and top member 20 are hinged to each other by a hinge means, here shown in the form of hinge pins 13a on the base member 13 and hinge members 20a on the top member 20. The hinge permits the top member 20 and base member 13 to be folded so that the opposed surfaces are basically against each other, in the position as shown in FIGS. 1 and 2.

The top member 20 has a pair of lens engaging means thereon in the form of ribs 24 extending at right angles to each other, and positioned on the surface of the top member 20 which will be opposed to the top surface of the base member 13 when the top member 20 and the base member 13 are folded together, and opposed to the lens receiving baskets 21, so as to enable contact lenses placed in the lens receiving baskets 21 to be held in position in the lens and catalyst block holder 12.

Means is provided on the base member and top member for securing them in the folded over condition, and in the embodiment of FIGS. 1-4, this means is comprised of a closure member 26 depending from the free edge of the top member 20 opposite the edge having the hinge members 20a thereon, which is engageable with a closure member receiving recess 27 in the corresponding edge of the base member 21. As can be seen from FIG. 3, the outwardly facing surface of the recess 27 has a sharp break 28 therein, and the inwardly facing surface of the closure member 26 has a nose 29 thereon which fits under the sharp break 28 for holding the top and base members 20 and 13 in the closed or folded over position.

The contact lens disinfection unit has a means for holding a catalyst block 34 in a position for circulation of a disinfectant solution from the space 15 within the container 10 over the catalyst block 34. In the embodiment of FIGS. 1-6, this means is constituted by a catalyst block cover 30 which is hinged by a hinge 31 integral with the top member 20 along one edge thereof, and having a closure retainer 32 at the opposite edge thereof engaged in a recess 33 in the top member 20 for holding the catalyst block cover in place. The catalyst block cover has a shape for defining with the outer surface of the top member 20 a catalyst block recess 33. Openings 37 are provided in the catalyst block cover 30 for permitting circulation of disinfecting solution through the space 33 over the surfaces of the catalyst block 34. In the present embodiment, these openings are provided in the end walls of the cover 30.

The catalyst block 34 as shown in FIGS. 1-6 is constituted by a block base 35 and ribs 36 which project in opposite directions from the base 35, and which extend generally longitudinally of the top member 20. The size is such that the cover 30 engages the outer ends of the ribs 36 and presses the catalyst block 34 against the outer surface of the cover 30 for holding it in position in the space 33.

The openings 37 in the catalyst block cover 30 can have different shapes and can be located anywhere in the cover so long as they permit circulation of the disinfecting solution along the base 35 and ribs 36 of the catalyst block.

Further, the catalyst block need not have the exact shape as shown, but can have any convenient shape, and the catalyst block cover can be given a shape such that it will hold the catalyst block against the outer surface of the top member 20.

While the catalyst block has been shown as being held against the outer surface of the top member 20, it can, alternatively be on any other part of the lens and catalyst block holder 12 where it will not interfere with the baskets 21.

Figure 3:
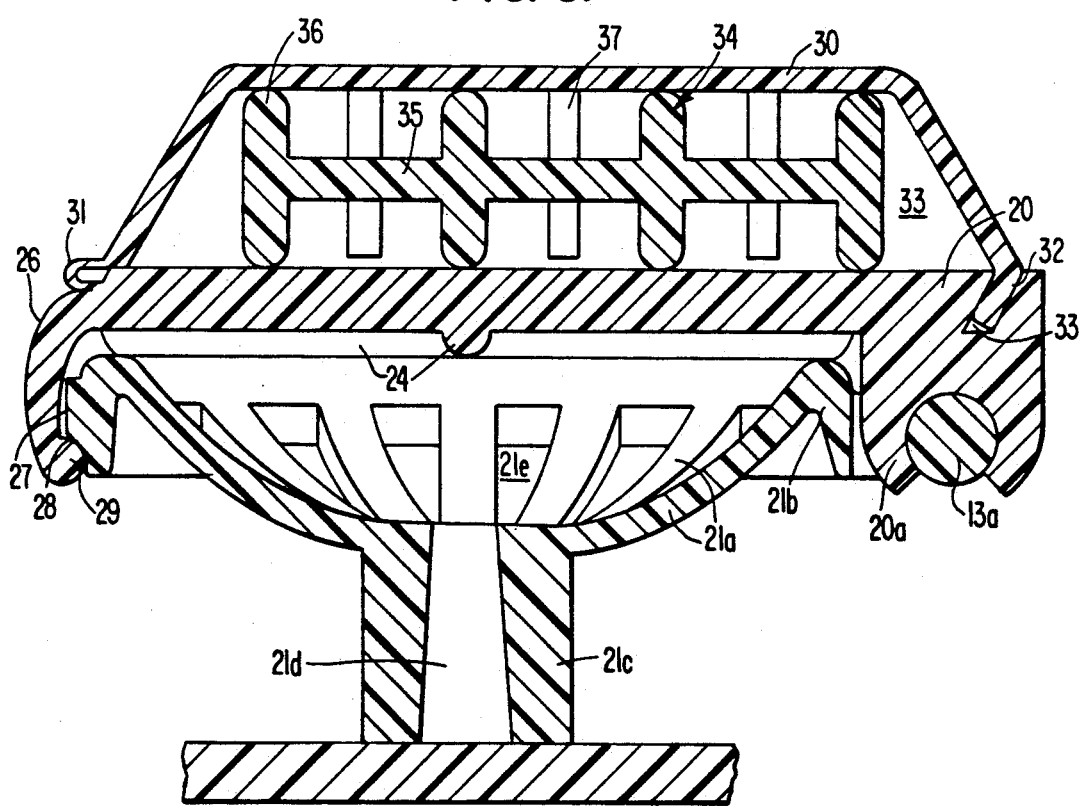
FIG. 3 is a section taken along line 3—3 of FIG. 2.
Figure 4:
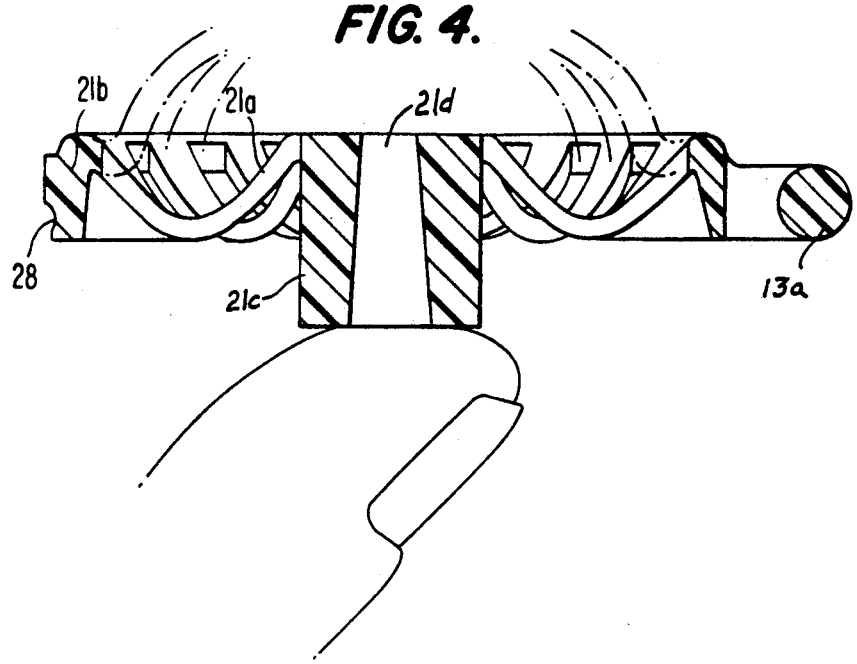
FIG. 4 is a view similar to FIG. 3 with the lens basket in the partially inverted position.
Figure 6:
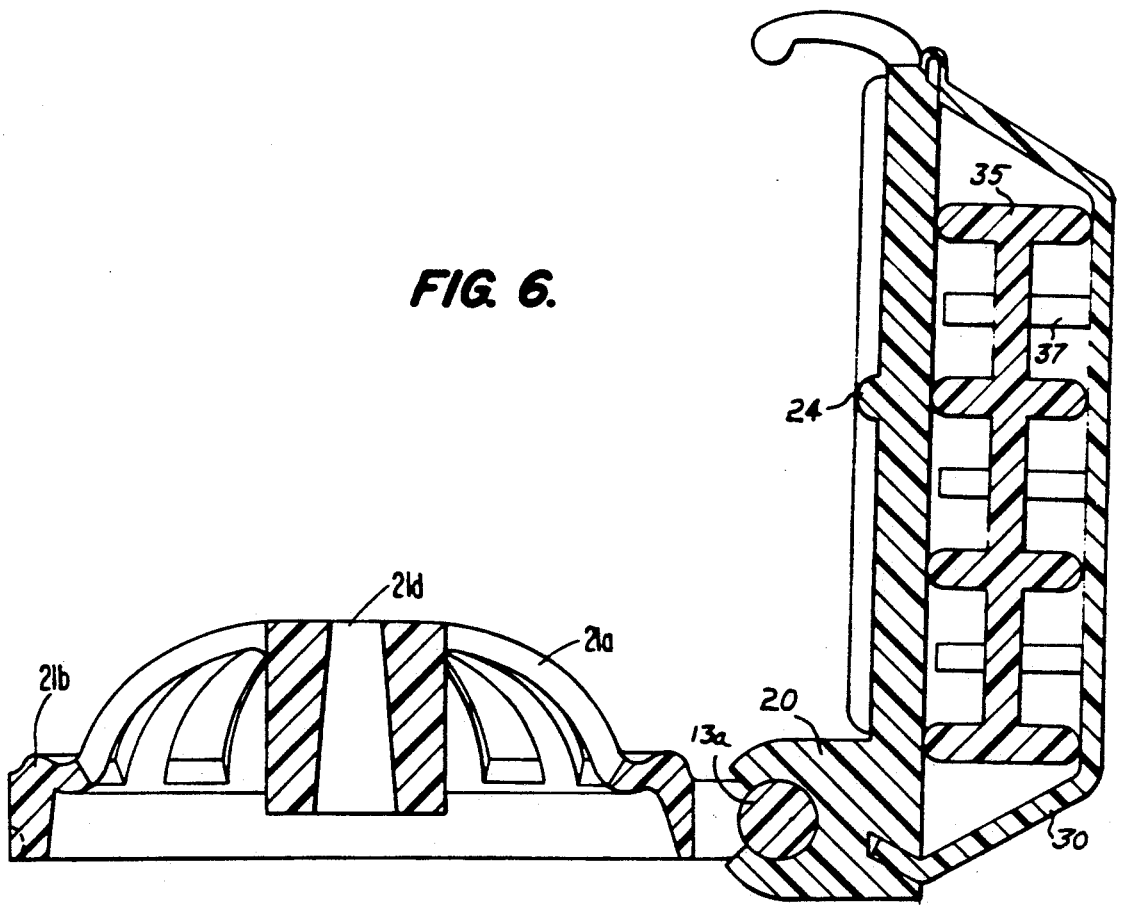
FIG. 6 is a transverse sectional view taken along line 6—6 of FIG. 5.
Figure 5:
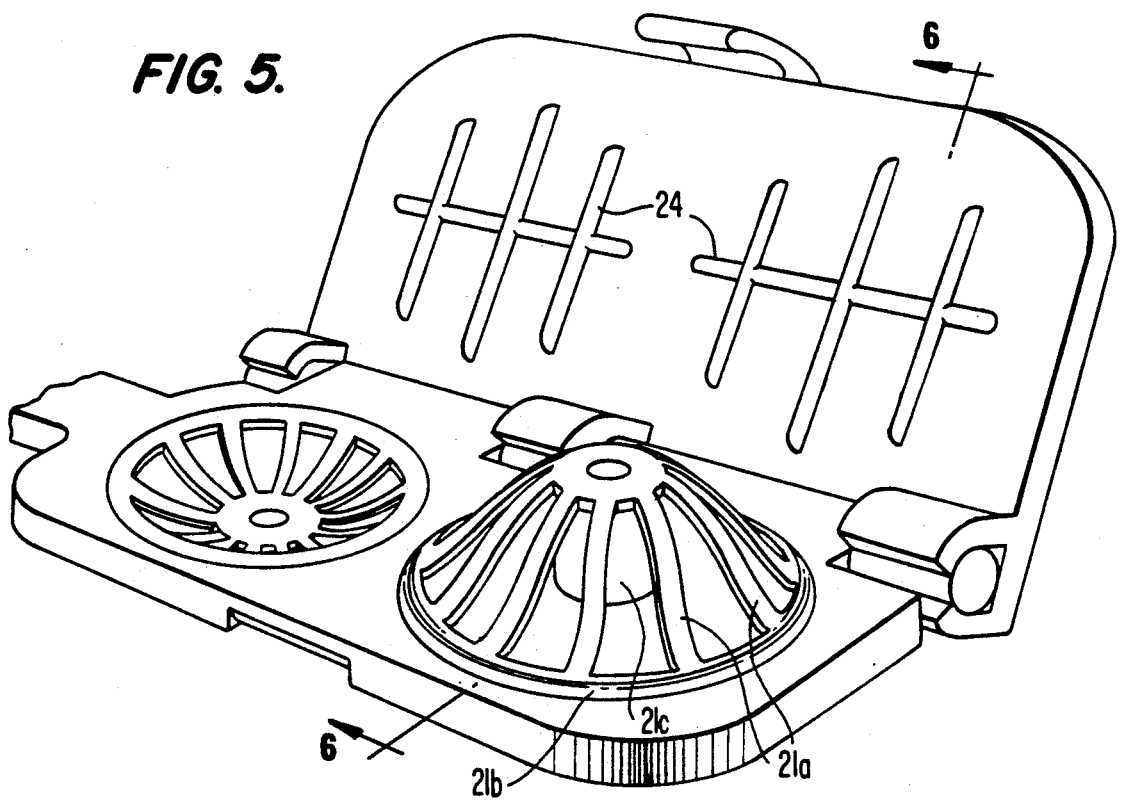
FIG. 5 is a view similar to FIG. 2 of a lens and catalyst block holder according to the invention with the top member open and one of the lens baskets inverted.

Each of the lens baskets 21 is comprised of a plurality of annularly spaced downwardly and inwardly curved ribs 21a made of a resilient flexible material, such as plastic, which extend from an annular frame member 21b which is mounted in a hole 16, either integral with the base member 13 or attached thereto, to a central hub member 21c preferably having a central longitudinal aperture 21d therethrough. The ribs 21a, the frame member 21b and the hub member 21c are preferably all molded from a single material such as plastic. The basket 21 can, because of the provision of the ribs 21a and the material thereof, be inverted from the concave lens receiving position shown in FIGS. 2 and 3 to the convex lens discharge position as shown in FIGS. 5 and 6 by passing through the position shown in FIG. 4. The hollow hub member 21c preferably, when the basket is in the concave lens receiving position as shown in FIGS. 2 and 3, engages the inside surface of the wall of the container 10, and serves not only as the structural member to tie the ends of the ribs together, but also as a finger grip for the user to move the basket from the lens receiving position to the lens discharge position during use of the unit, as will be described more fully thereinafter. The spaces 21e between the ribs and the central aperture 21d through the hub member 21c serve to circulate disinfecting solution over the convex face of a contact lens which is held in the basket 21.

In use, the catalyst block 34 is provided in the catalyst block space 33, and has a catalyst (not shown) coated thereon which, when the disinfecting solution is passed over the catalyst, will neutralize the disinfecting solution. The cap 11 is removed from the container 10, thus drawing the lens and catalyst block holder 12 out of the container 10, and the top member 20 is pivoted away from the base member 13 by releasing the closure member 26, thus opening the top member to the position as shown in FIG. 4. The lens receiving baskets 21 are moved to their concave positions and contact lenses are placed with the convex sides down in the lens receiving baskets 21, and the top member 20 is then closed and the closure member 26 engaged with the closure member receiving recess 27.

The container 10 is then substantially filled with the disinfecting solution, and the lens and catalyst block holder 12 is inserted into the container 10 and the cap 11 engaged with the container.

The disinfecting solution flows around the contact lenses through the spaces 21c of the baskets 21, and past the ribs 24, disinfecting the lenses. It also comes in contact with the catalyst on the catalyst block 34, and the neutralization starts. In the typical system, neutralization produces gas, which tends to raise to the top of the container 10 when the container is in its normal position, i.e. standing upright with the cap 11 at the top. This induces circulation of the disinfecting solution downwardly along the base member 13 and the face of the top member 20 facing the base member 13, and over the surfaces of the contact lenses held between the ribs 21a of the baskets 21 and the ribs 24. The circulation is further induced over the surfaces of the block ribs 36 and the block base 35 along the surfaces thereof, by the flow of the disinfecting solution through the circulating openings 37. At such time as the neutralization is complete, generation of gas will cease, and the lenses will then be ready for insertion into the eyes.

A gas escape groove 38 can be provided in the open end of the container 10 for escape of gasses during the neutralization process.

Then the cap 11 is removed from the container 10 and the top member 20 turned back to the position as shown in FIG. 5. The hub members 21c are then grasped between the fingers of the user, or pressed by the finger of a user, as shown in FIG. 4, to invert them from the concave lens receiving position of FIGS. 2 and 3 through the position of FIG. 4 to the position of FIG. 6. In FIG. 5, only one basket is shown as having been moved to the inverted position. As will be readily understood, this will lift the contact lens which has been resting in the basket 21 in the concave condition, and cause it to rise out of the basket, thereby making it easy to grasp it and remove it from the unit. The baskets can then be returned to the concave position ready for use again.

As is clear from FIG. 6, the end of the ribs 21a where they are joined to the frame member 21b, are sharply bent when the basket is fully inverted. The resiliency of the material is made such that in this condition the basket will remain inverted, but only a small force starting it toward the normal shape is required, and the energy stored in the sharply bent ribs will carry the basket to the normal condition as shown in FIG. 3.

Figure 7:
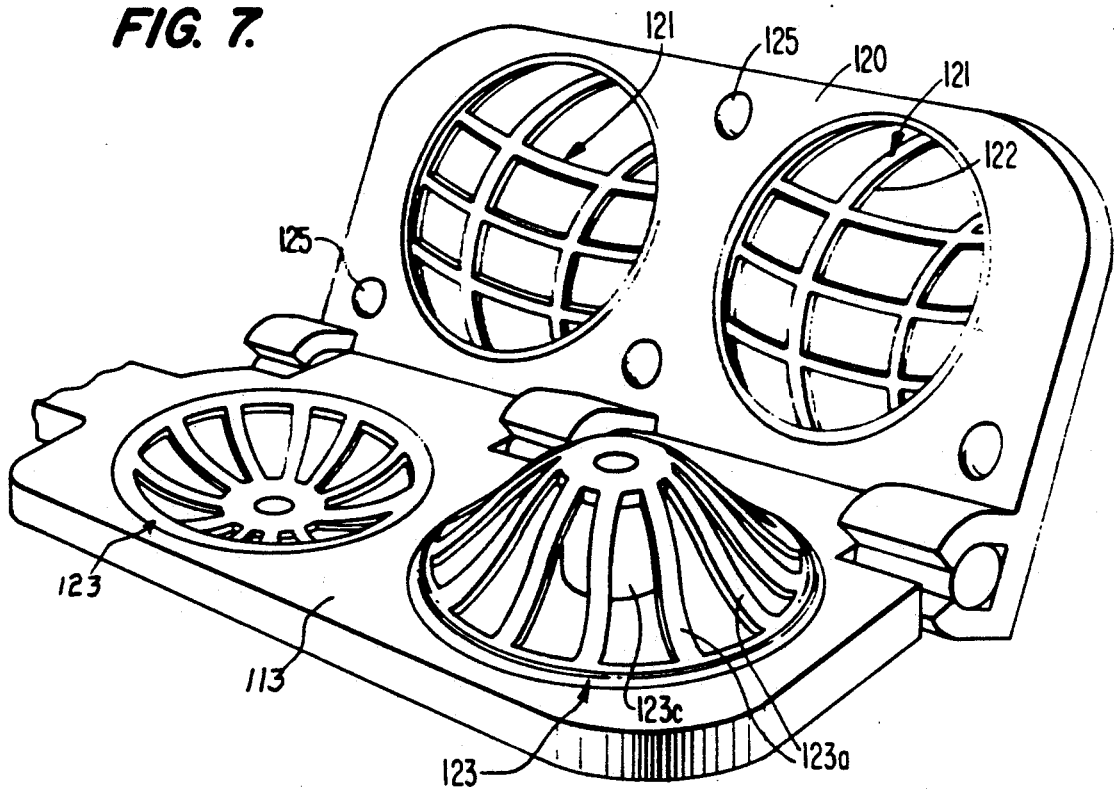
FIG. 7 is a perspective view similar to FIG. 5 of a contact lens disinfection unit according to a second embodiment of the invention.

As shown in FIG. 7, the means for engaging the pair of contact lenses in both the base member and the top member can be lens receiving baskets. As shown, the base member 113 has two apertures therein, in which are provided invertible lens engaging baskets 123 with the flexible ribs 123a as in the embodiment of FIGS. 1-6. At corresponding positions on the top member 120 are lens receiving baskets 121 having grid members 122 which are convex with respect to the face of the top member 120 which faces the base member when the members are folded together. The grid members 122 are, when the members 113 and 120 are folded together, spaced slightly from the ribs 123a so as to accommodate contact lenses therebetween. This spacing is insured by a plurality of spacing knobs 125 on the surface of the top member 120 facing the upper surface of the base member 113.

As will be appreciated, the lens baskets 123 and 121 can be interchanged, i.e. the concave lens baskets 121 can be provided in the base member 113, and the inverted baskets 123 can be provided in the top member 120. Likewise, the spacing knobs 125 can be provided on either of the faces of the base member or the top member which is opposed to the other member when the members are folded together.

The use of this embodiment is the same as the embodiment of FIGS. 1-6, except that the disinfecting solution will circulate through the lens engaging baskets 121 in the top member into the space 33 in which the catalyst block is located.

In both embodiments, when the catalyst coated on the catalyst block is exhausted, the catalyst block can be replaced by opening the cover 30.

Figure 8:
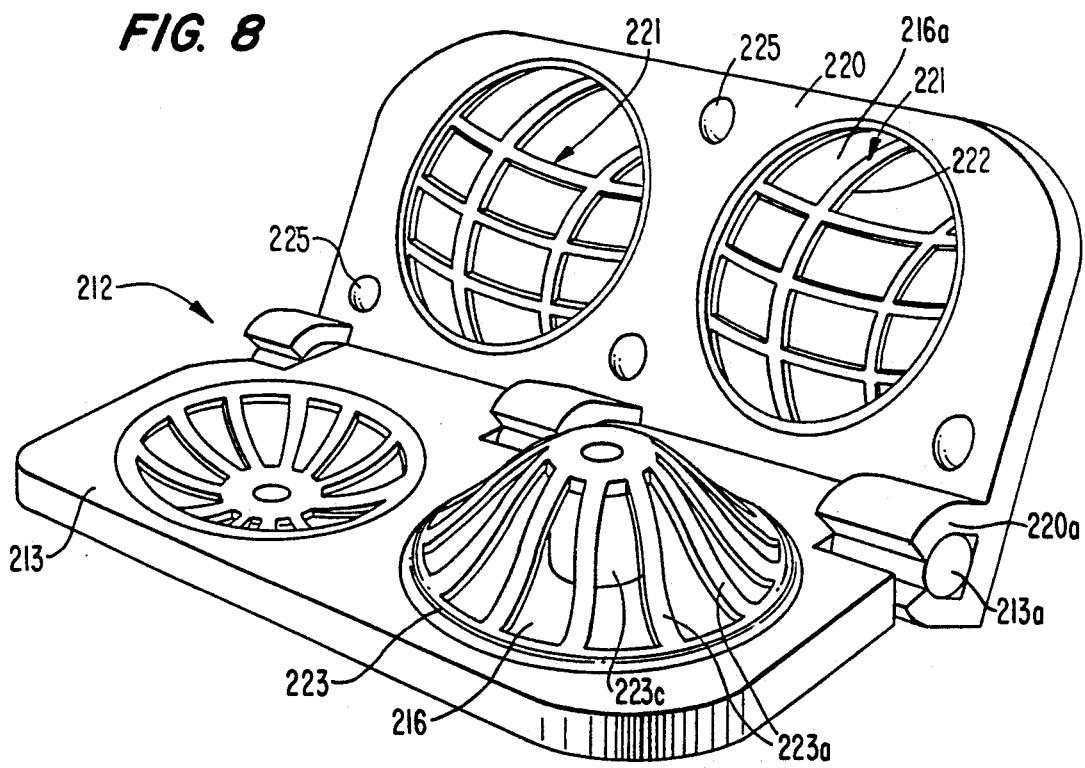
FIG. 8 is a perspective view of a contact lens holder for use in a contact lens disinfection unit.

A separate lens holder 212 is shown in FIG. 8 which can be used with a different type container. It is comprised of a base member 213 which has a pair of holes 216 therethrough which contain a pair of lens engaging means in the form of lens receiving baskets 223 the same as baskets 21 in FIGS. 1-6 and which extend concavely from the surface of the base member 213 which is uppermost in FIG. 8. The lens receiving baskets 223 are constituted by a plurality of flexible ribs 223a and hub members 223c.

The lens holder further comprises a top member 220, and the base member 213 and top member 220 are hinged to each other by a hinge means, here shown in the form of hinge pins 213a on the base member 213 and hinge members 220a on the top member 220. The hinge permits the top member 220 and base member 213 to be folded so that the opposed surfaces are basically against each other, similar to the position of the embodiment of FIGS. 1-4 as shown in FIGS. 1 and 2.

The top member 220 has a pair of holes 216a in which are lens engaging means thereon in the form of lens receiving baskets 221 which extend convexly in the surface of the top member. The lens receiving baskets 221 are constituted by a plurality of grid members 222 intersecting each other at generally right angles. The baskets 221 are opposed to the baskets 223 in the top surface of the base member 213 when the top member 220 and the base member 213 are folded together, and the opposed lens receiving baskets 221 and 223 are spaced slightly so as to hold contact lenses placed in the lens receiving baskets in position.

Means can be provided on the base member and top member for securing them in the folded over condition, which is preferably the same as the means 26 and 27 in the embodiment of FIGS. 1-4. Moreover, means in the form of knobs 225 can be provided on one of the members, for example the top member 220, which, when the members 213 and 220 are folded together, keep the baskets 221 and 223 spaced slightly so as to accommodate the lenses therebetween.

Similarly the contact lens holder can have a means (not shown) on top member 220 for holding a catalyst block similar to the catalyst block 34 in FIGS. 1-4 in a position for circulation of a disinfectant solution over the catalyst block and through the baskets 223 over the lenses. Alternatively the catalyst block can be on the back of the base member 213.

Where the holder has no means for holding a catalyst block, it can be used in a container of any shape which has a catalyst block therein.

The embodiment shown in FIGS. 9-12 is of a contact lens disinfection unit which is rather different from that of the embodiments of the earlier figures, but which also is able to use the invertible basket.

The embodiment comprises a generally cylindrical disc-shaped container 40 having an upstanding side wall 41 from the upper edge of which projects a flange 42 in which are bayonet-joint recesses 43. A ridge 44 extends around the inside of the bottom of the container, and in the space between the ridge 44 and the upstanding wall 41 is provided a sealing gasket 45. A cover 46 is provided which has a depending flange 47 depending from a position spaced inwardly from the peripheral edge of the cover 46, and projecting from the flange are bayonet-joint projections 48 which, when the cover is inserted into the container 40, and is turned, align with the recesses 43, so that the cover can fit down into the container 40. Further turning of the cover then moves the projections 48 under the flange 12 to prevent removal of the cover. This also urges the lower end of the depending flange 47 into the sealing gasket 45 to provide a seal for the contents of the container.

Positioned at side-by-side positions in the bottom of the container are two sockets 49, each of which is to hold the hub member 51c of an invertible basket 51 mounted on the upper end of the base member 51c. The invertible basket has the same construction as the invertible basket of the earlier described embodiments, i.e. it has an annular frame member 51b and a plurality of annularly spaced downwardly and inwardly curved ribs 51a made of a resilient flexible material and extending from the frame member 51b to the hub member 51c. The hub member 51c is frictionally engaged in the socket 49 so that it will not normally fall out if the container is turned upside down, but nevertheless it can be removed by a moderate amount of force exerted on the invertible basket 51.

The two baskets thus provided are for a left lens and a right lens, and covers are provided which normally cover the baskets to hold the lens in the baskets. To this end, two pairs of posts 60 are provided projecting upwardly from the bottom of the container 40, and to the top of a first pair of posts is hinged a cover 61 having arms 62 extending from the cover proper to the posts 60, and pivoted on the posts by a shaft 63. A second cover 64 is provided which has similar arms 65 pivoted to the other pair of posts by shafts 63a.

Figure 10:
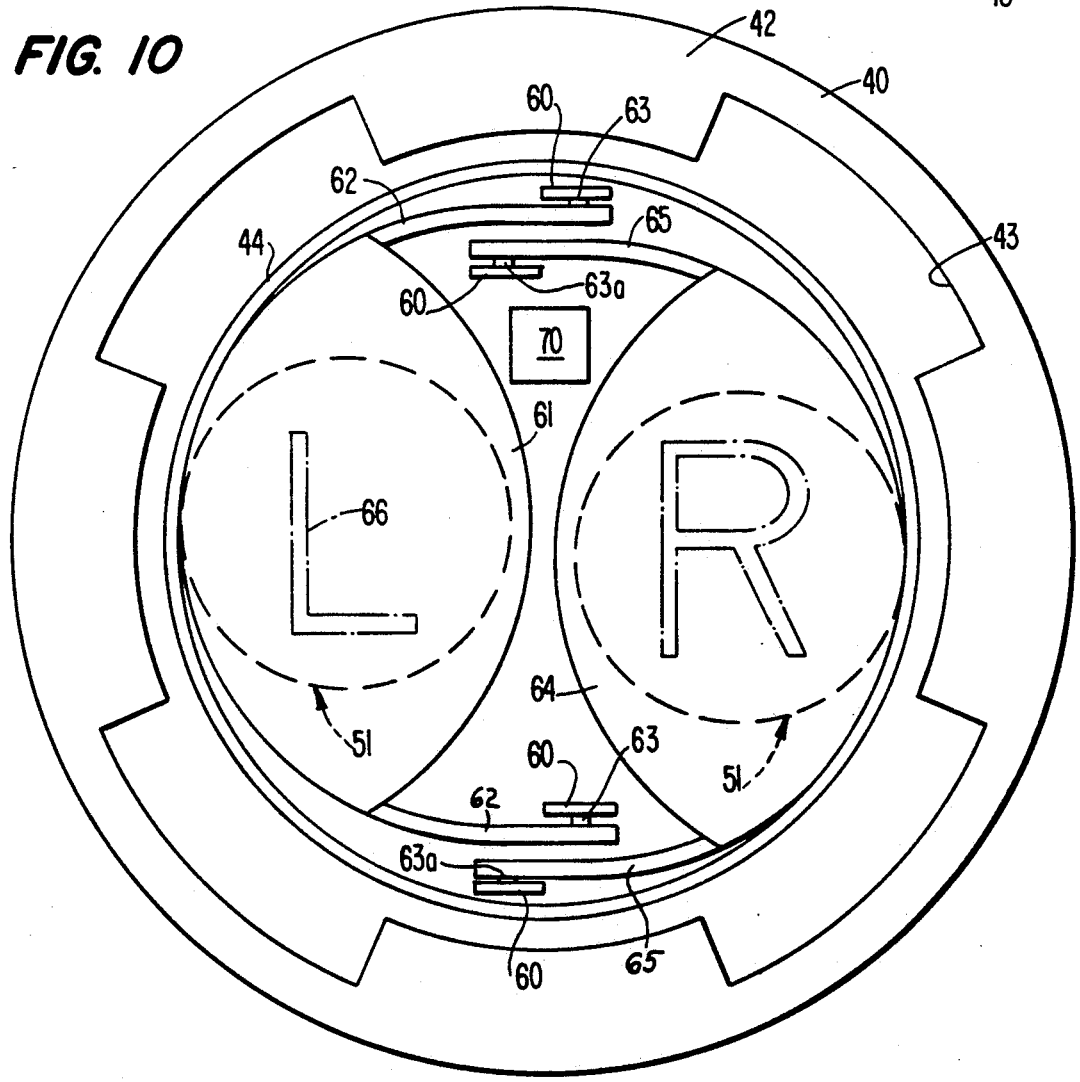
FIG. 10 is a top plan view of the container portion thereof with the cover removed.
Figure 12:
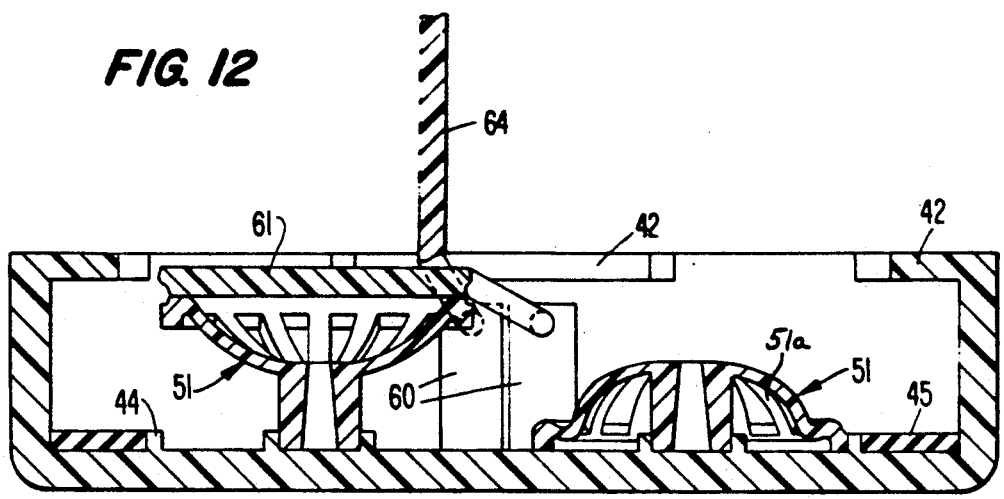
FIG. 12 is a view similar to FIG. 9 with one cover turned back and one lens basket inverted.

It will be seen from FIGS. 10 and 12 that the arms 62 and 65 are preferably arranged so that on one side of the container the arm for the one cover is outside of the arm for the other cover, and at the other side of the container, the arm for the one cover is inside the arm for the other cover. This permits positioning of the posts further away from the position of the baskets so as to enable the arms to be made longer thus enabling the covers to be lifted higher and further away from the baskets.

Figure 9:
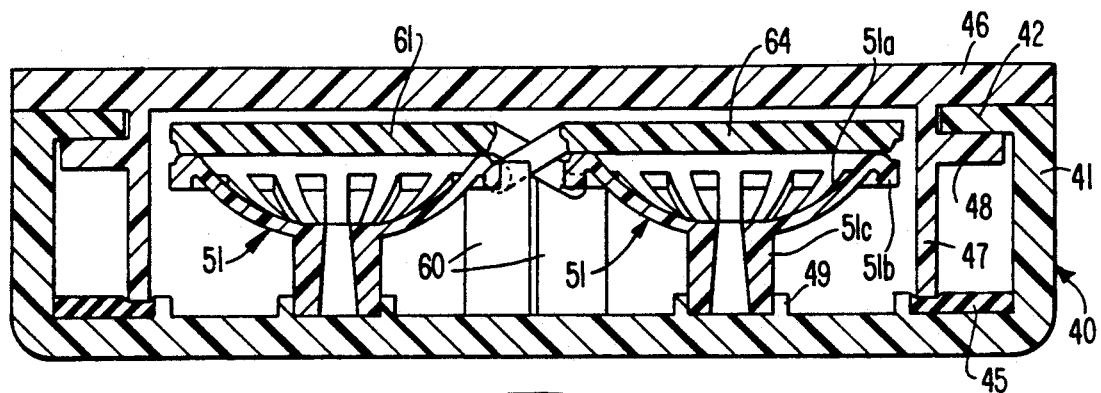
FIG. 9 is a sectional view of a third embodiment of the lens disinfection unit according to the invention.
Figure 11:
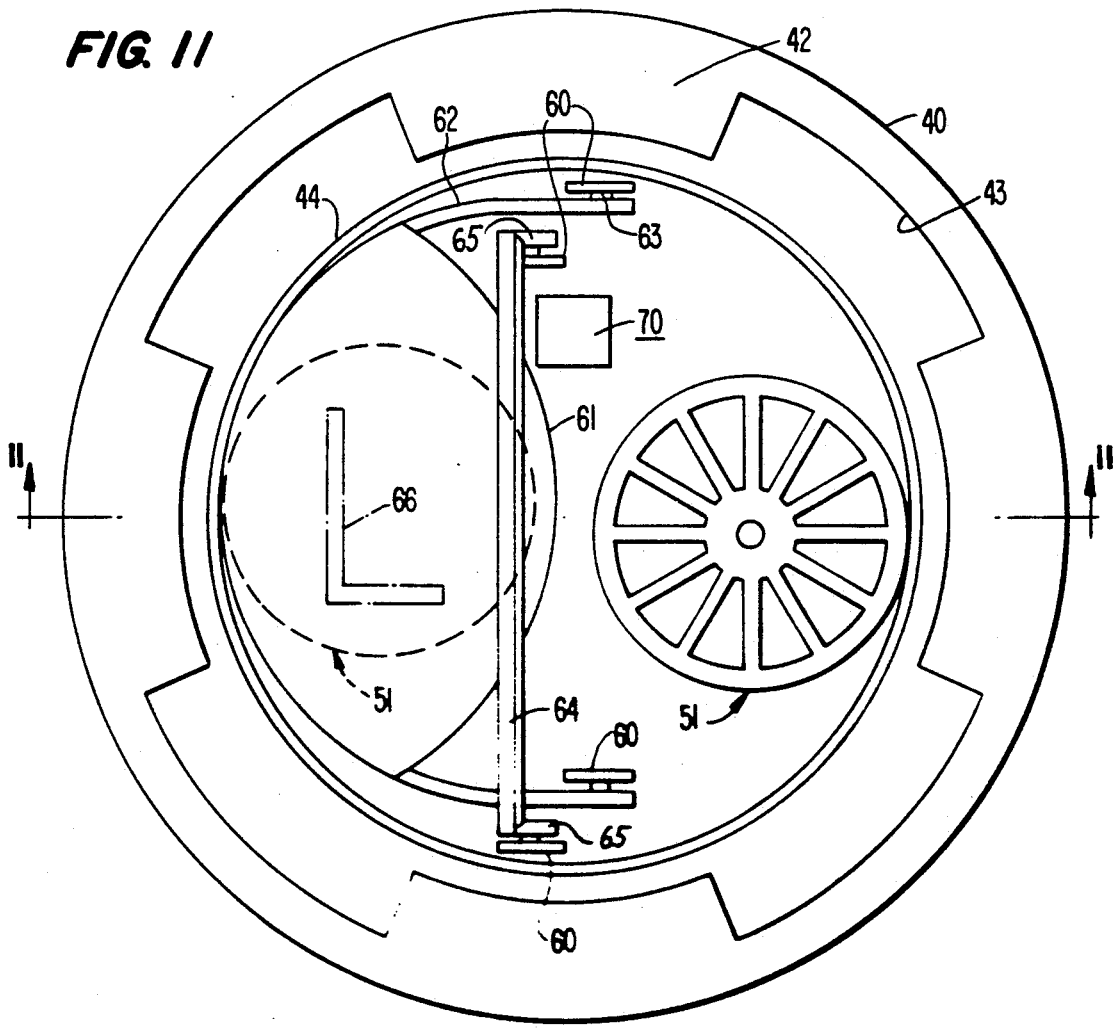
FIG. 11 is a view similar to FIG. 9 with one of the covers turned back.

As can be seen, the covers, when in the lowered position of FIGS. 9 and 10, cover the baskets 51. Upon pivoting the one cover 61, the cover is raised upwardly and to the right in FIG. 10, as shown in FIG. 11, thus exposing the basket 51 therebeneath.

A catalyst block 70 is positioned in the container, and is preferably removably held on the bottom of the container.

In use, with the container cover 46 removed, the cover 61 is raised and one of a pair of contact lenses is placed with the convex side down into the basket 51 therebeneath. In the particular embodiment shown, the left lens should be placed in the basket, since an indicia 66 indicating the left lens is preferably provided on the cover 61. The cover is then lowered, and the cover 64 raised and the right contact lens placed in the basket beneath the cover 64. The cover 64 is then lowered.

With a still functioning catalyst block 70 in position, the container is then filled with a disinfecting solution, and the container cover is then placed on the container and manipulated so as to close the container cover and hold it in the closed position by the bayonet-joint, at which time the container will be sealed by the engagement of the bottom of the flange 47 with the gasket 45. The disinfecting solution then circulates over the lenses through the apertures in the baskets, and the solution is neutralized by the catalyst on the catalyst block 70.

After a predetermined period of time, when the amount of solution placed in the container has been neutralized, the container cover is removed, and the solution is poured out of the container. Thereupon, one of the covers is raised, and the annular frame 51b of the thus exposed basket is engaged by the fingers of the user and the basket is inverted to the position as shown in FIG. 11. At this point, the lens will be freed from the ribs 51a of the basket and the annular frame, and will be easily grasped by the fingers of the user to lift it from the inverted basket. Thereafter, the cover 61 is lowered, the cover 64 raised, and the procedure repeated for the other lens.

Figure 13:
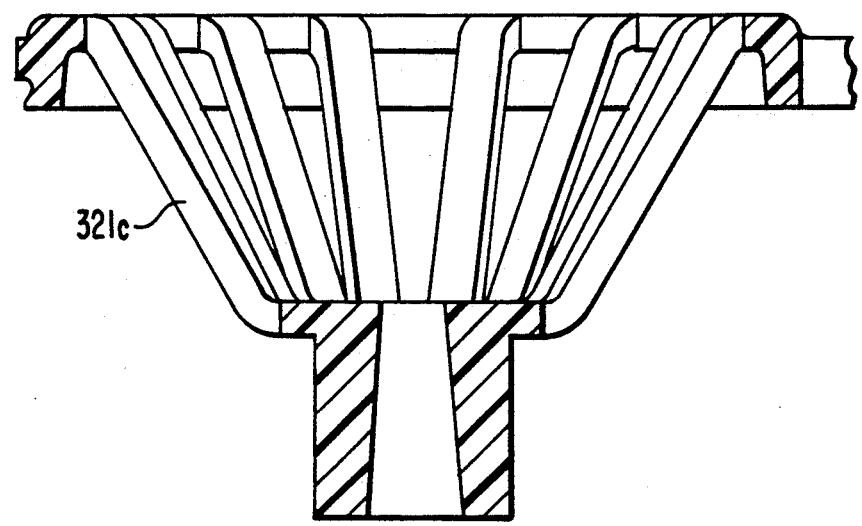
FIG. 13 is a sectional view of a modified form of the invertible basket.
Figure 14:
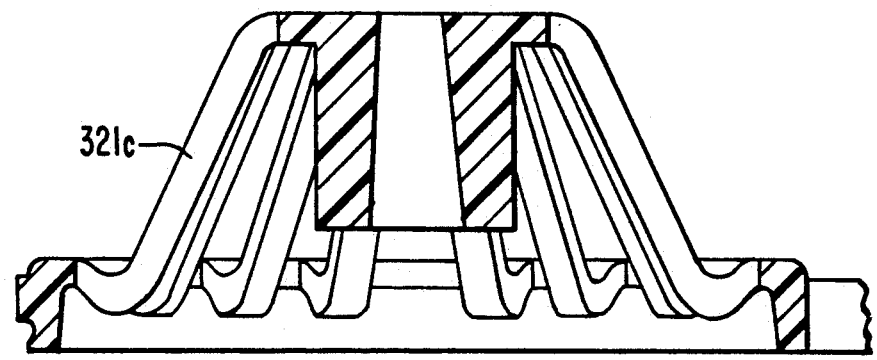
FIG. 14 shows the basket of FIG. 13 in an inverted condition.

The shape of the basket in its normal condition has been shown throughout the drawings as being generally spherically concave. However, other forms and shapes are possible. For example, as shown in FIG. 13, the ribs 321c can be given a generally straight shape, which gives a generally trapezoidal cross-sectional shape to the basket. The ribs retain their generally straight shape when the basket is inverted, as shown in FIG. 14.

Figure 15:
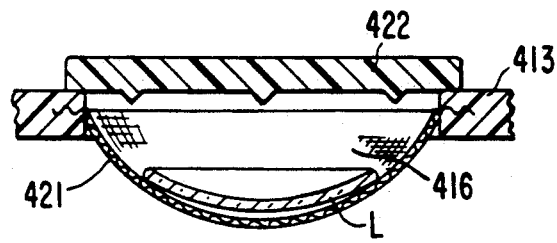
FIG. 15 is a sectional view of a further modified form of the invertible basket.
Figure 16:
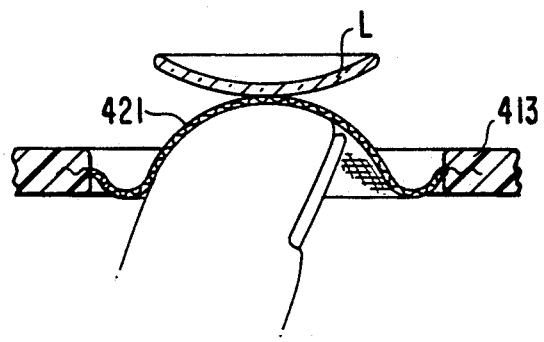
FIG. 16 shows the basket of FIG. 13 in an inverted condition.

The baskets can be formed by structure other than the frame member, the ribs and the hub member. As shown in FIGS. 15 and 16, the basket can be formed of a resilient flexible woven mesh screen or fabric 421, preferably of flexible resilient plastic material, such as nylon or propylene, the edges of which are molded or otherwise fastened into the edges of an opening 416 in a plate 413 the same as or similar to that shown for example in FIGS. 5, 7 and 8, or in some similar structure. As with the basket formed of the ribs and hub member, the basket of woven fabric can be inverted by pressure applied by the finger, as shown in FIG. 16 to bring the lens L to a position where it can be easily grasped to remove it from the basket. Where the plate 413 is not part of a structure with a top member hinged thereto, such as in FIGS. 5, 7 and 8, a cover 422 can be provided which covers the top of the opening to protect and retain the lens L therein.

Figure 17:
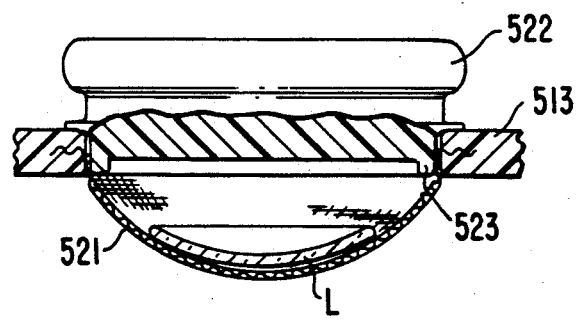
FIG. 17 is a sectional view of a still further form of the invertible basket.
Figure 18:
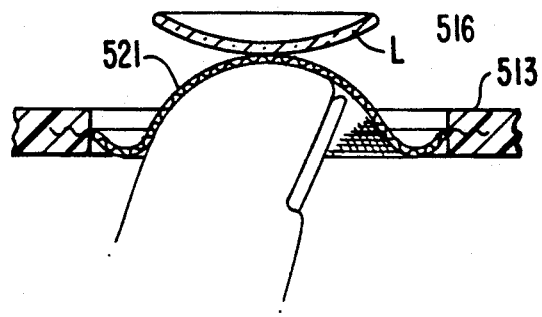
FIG. 18 shows the basket of FIG. 17 in an inverted condition.

It is not necessary that the material of the basket be resilient. An example of a non-resilient mesh screen or woven fabric which forms the basket is shown in FIGS. 17 and 18, in which the woven material 521 has the edges molded or otherwise fastened into the edges of an opening 516 in a plate 513 the same as or similar to that shown in FIGS. 5, 7 and 8, or in some similar structure. The basket can be easily inverted by finger pressure as shown in FIG. 16. Where the plate 513 is not part of a structure with a top member hinged thereto, such as in FIGS. 5, 7 and 8, a cover 522 can be provided which covers the top of the opening. The cover 522 preferably has an outwardly flared rib 523 which frictionally fits into the opening 516 or snaps into the opening to retain the cover 522 in position.

It will be seen that by the use of the invertible basket, together with the means for holding the lens in the basket, the lens is held firmly during the time the solution is caused to pass over it for disinfecting the lens, but when the time comes to remove the lens from the basket, the basket is easily invertible so that the edges of the lens can be easily grasped to lift the lens from the inverted basket.

What is claimed is:

1. A contact lens holding unit comprising:
   a container;
   a cap detachably mounted on said container;

a lens holder mounted in said container and extending into said container, said lens holder including at least one lens basket for receiving a contact lens therein for holding the contact lens with the surfaces thereof exposed to the space around said holder, said at least one lens basket being flexibly invertible between a concave position in which it holds a lens positioned with the convex side against the lens basket and a convex position in which it pushes the lens out of the basket.

2. A contact lens holding unit as claimed in claim 1 further comprising a catalyst block positioned in said container, whereby when a disinfection solution which is decomposed is placed in said container for disinfecting a lens held in said lens holder, said catalyst block begins decomposition of the solution.

3. A contact lens disinfection unit comprising:
a container;
a cap detachably mounted on said container;
a lens and catalyst block holder mounted on and depending from said cap and extending into said container when said cap is mounted on said container, said holder having at least one lens basket for receiving a contact lens therein for holding the contact lens with the surfaces thereof exposed to the space around said holder, said at least one lens basket being flexibly invertible between a concave position in which it holds a lens positioned with the convex side against the lens basket and a convex position in which it pushes the lens out of the basket; and means for holding a catalyst block on said holder in a position for circulation of a disinfecting solution from the space around said holder over the catalyst block.

4. A contact lens disinfection unit as claimed in claim 3 in which said at least one lens receiving basket has a plurality of ribs of flexible resilient material extending downwardly and inwardly from the edge of the basket to the center thereof.

5. A contact lens disinfection unit as claimed in claim 3 in which said at least one lens receiving basket is a screen mesh of flexible resilient material extending downwardly and inwardly from the edge of the basket to the center thereof.

6. A contact lens disinfection unit as claimed in claim 3 in which said at least one lens receiving basket is a screen mesh of a flexible non-resilient material extending downwardly inwardly from the edge of the basket to the center thereof.

7. A contact lens disinfection unit as claimed in claim 3 in which said lens and catalyst block holder comprise a base member having a pair of said lens receiving baskets thereon, a top member having a pair of lens engaging means thereon for engaging a pair of contact lenses, said base member and said top member being hinged to each other and said pair of lens engaging means on said top member and said pair of lens receiving baskets on said base member being opposed to respective one of each other when said base member and said top member are folded against each other for holding a pair of contact lenses therebetween, means on one of said base member and said top member for engaging the other for securing in the folded condition, and said catalyst block holding means being positioned on one of said base member and said top member.

8. A contact lens disinfection unit as claimed in claim 7 in which said pair of lens engaging means on said top member comprises a pair of sets of ribs projecting from the bottom surface of said top member which opposes the top surface of said base member when said top member and said base member are folded against each other, said pair of sets of ribs being opposed to respective ones of said pair of baskets when said top member and said base member are folded against each other.

9. A contact lens disinfection unit as claimed in claim 7 in which said pair of lens engaging means on said top member comprises a pair of lens receiving baskets having a plurality of grid members extending convexly from the bottom surface of said top member which opposes the top surface of said base member when said top member and said base member are folded against each other and having spaces therebetween, respective ones of said pair of baskets being opposed to each other when said top member and said base member are folded against each other.

10. A contact lens disinfection unit as claimed in claim 7 in which said catalyst block holding means comprises a catalyst block cover detachably engaged with said top member and defining a space within said cover when said cover is engaged with said top member for holding a catalyst block therein, said cover having means defining apertures therein for permitting circulation of a disinfectant through said space.

11. A contact lens disinfection unit as claimed in claim 10 in which said catalyst block cover is hinged at one side to said top member and includes closure means for holding the other side of said catalyst block cover to said top member.

12. A contact lens disinfection unit as claimed in claim 7 in which said top member has spacing knobs on the bottom surface thereof for engaging the top surface of said base member for slightly spacing said baskets from each other for accommodating contact lenses therebetween.

13. A contact lens holder for holding contact lenses in a disinfection unit, comprising: a first member and a second member hinged to said first member, said members being foldable together, said first member having at least one invertible lens receiving basket normally extending concavely from the surface of said first member which faces the second member when said members are folded against each other and being flexibly invertible between a concave position and a convex position, and said second member having at least one lens engaging basket having a plurality of grid members extending convexly from the surface of said second member which opposes said first member when said members are folded against each other and having spaces therebetween, respective ones of said lens receiving baskets and said lens engaging baskets being opposed to each other when said first and second members are folded against each other.

14. A contact lens holder as claimed in claim 13 in which there is a pair of lens receiving baskets on said first member and a pair of lens engaging baskets on said second member.

15. A contact lens holder as claimed in claim 14 in which each of said first and second members has means defining a pair of holes therethrough in which respective ones of said lens engaging baskets and said lens receiving baskets are positioned.

16. A contact lens holder as claimed in claim 13 in which said at least one invertible lens receiving basket has a plurality of ribs of flexible resilient material extending downwardly and inwardly from the edge of the basket to the center thereof.

17. A contact lens holder as claimed in claim 13 in which said at least one lens receiving basket is a screen mesh of flexible resilient material extending downwardly and inwardly from the edge of the basket to the center thereof.

18. A contact lens holder as claimed in claim 13 in which said at least one lens receiving basket is a screen mesh of a flexible non-resilient material extending downwardly and inwardly from the edge of the basket to the center thereof.

19. A contact lens holder as claimed in claim 13 in which said one of said first and second members has spacing knobs on the surface thereof for engaging the exposed surface of said other of said first and second members for slightly spacing the respective ones of said lens receiving baskets and said lens engaging baskets from each other for accommodating contact lenses therebetween.

20. A contact lens holder as claimed in claim 13 further having a catalyst block holding means on the side of one of said first and second members which faces away from the other of said first and second members when the first and second members are folded against each other.

21. A contact lens disinfection unit comprising:
   a container;
   a cap detachably mounted on said container;
   at least one lens holder mounted in said container and extending into the interior of said container, said at least one lens holder having a mounting hub mounted on the inside of said container and said hub having a free end with a lens basket thereon for receiving a contact lens therein, said lens basket being flexibly invertible between a concave position in which it holds a lens positioned with the convex side against the lens basket and a convex position in which it pushes the lens out of the basket; and
   a catalyst block in said container for permitting a disinfectant solution which is placed in said container to circulate around the holder and the catalyst block.

22. A contact lens disinfection unit as claimed in claim 21 in which said hub is removably mounted on the inside of said container.

23. A contact lens disinfection unit as claimed in claim 21 further comprising a cover member mounted on said container and pivotable from a position in which it covers said lens basket to a position in which said lens basket is uncovered.

24. A lens holder for holding a contact lens for storage or for disinfection, comprising a lens basket which is flexibly invertible between a concave position in which it holds a lens positioned with the convex side against the lens basket and a convex position in which it pushes the lens out of the basket.

25. A lens holder as claimed in claim 24 in which said holder further comprises a hub member and said basket comprises an annular frame member and a plurality of annularly spaced downwardly and inwardly extending ribs made of a resilient flexible material extending from said frame member to said hub member.

26. A lens holder as claimed in claim 24 in which said lens basket is a screen mesh of flexible resilient material extending downwardly and inwardly from the edge of the basket to the center thereof.

27. A lens holder as claimed in claim 24 in which said lens basket is a screen mesh of a flexible non-resilient material extending downwardly and inwardly from the edge of the basket to the center thereof.

* * * * *